United States Patent [19]

Eckler

[11] Patent Number: 4,709,104
[45] Date of Patent: Nov. 24, 1987

[54] CRYSTALLIZATION-INHIBITED TRIMETHYLOLETHANE SOLUTIONS

[75] Inventor: Paul E. Eckler, Terre Haute, Ind.

[73] Assignee: International Minerals & Chemical Corp., Terre Haute, Ind.

[21] Appl. No.: 787,621

[22] Filed: Oct. 15, 1985

[51] Int. Cl.$^4$ .................. C07C 29/94; C07C 31/22
[52] U.S. Cl. .................................. 568/853; 568/854
[58] Field of Search ............................ 568/853, 854

[56] References Cited

U.S. PATENT DOCUMENTS

| | | | |
|---|---|---|---|
| 2,270,839 | 1/1942 | Wyler | 568/854 |
| 2,292,926 | 8/1942 | Brubaker et al. | 568/853 |
| 2,304,985 | 12/1942 | Wyler | 568/854 |
| 2,400,724 | 5/1946 | Walker | 568/853 |
| 2,420,496 | 5/1947 | Poitras et al. | 568/854 |
| 2,671,118 | 3/1954 | Gsngwer | 568/854 |
| 2,790,837 | 4/1957 | Robeson | 568/853 |
| 3,076,854 | 2/1963 | Klein | 568/854 |
| 3,097,245 | 7/1963 | Russell et al. | 568/853 |

FOREIGN PATENT DOCUMENTS 808878  2/1959  United Kingdom ............... 568/854

OTHER PUBLICATIONS

Addadi et al., "Angen. Chem.", Int. Ed. Engl., 24, (1984), pp. 466–485.
Rogers et al., "J. Appl. Chem. Biotechnol", 24, (1974), pp. 171–180.
Clatworthy et al., "J. Appl. Chem. Biotechnol", 26, (1976), pp. 30–36.

Primary Examiner—J. E. Evans
Attorney, Agent, or Firm—Robert H. Dewey; Thomas L. Farquer

[57] ABSTRACT

Crystallization of trimethylolethane from supersaturated aqueous solutions is inhibited in the presence of effective amounts of crystallization inhibitors selected from methanol, isopropanol, s-butyl alcohol, t-butyl alcohol, 2-ethoxyethanol, 2-methoxyethanol, 1-methoxy-2-propanol, formic acid and 1-dimethylamino-2-propanol.

7 Claims, No Drawings

CRYSTALLIZATION-INHIBITED TRIMETHYLOLETHANE SOLUTIONS

BACKGROUND AND SUMMARY OF THE INVENTION

This invention relates to a method for inhibiting crystallization of trimethylolethane from supersaturated aqueous solutions thereof and to the crystallization-inhibited solutions prepared in accordance with that method.

Most commercial customers for industrial chemicals prefer to handle bulk raw materials in liquid form. Liquids can be handled economically in bulk by pumping and metering, thus avoiding the manual labor associated with transporting and opening solid-containing containers and weighing solid charges.

Trimethylolethane is a water soluble crystalline polyhydric alcohol which finds widespread use in the chemical industry particularly in the manufacture of alkyd resins, drying oils and plasticizers. Trimethylolethane (TME), while a crystalline solid in pure form, is for the above reasons advantageously shipped in bulk for commercial usage as its aqueous solutions. Of course, the more concentrated solutions can be made, the more cost efficient shipping and handling can be. Aqueous solutions of TME as concentrated as 80% solids can be shipped as heated solutions in insulated tank trucks. Aqueous solutions of trimethylolethane at 50% solids can be shipped (as solutions) so long as the outdoor temperatures do not drop below 0°–5° C.

The solubility profile of TME in water is such that any cooling of concentrated aqueous TME solutions can easily result in solution supersaturation and concomitant crystallization of TME from solution. Indeed, supersaturated solutions of TME can "crystallize" into a solid crystalline mass. Cooling of concentrated aqueous TME solutions in shipment, in storage tanks and in pumping and metering equipment can result in a plant manager's nightmare. There is little that can be done with the resulting solid crystalline mass once it forms in shipping containers or processing equipment except to find some way to heat the "mass" to again form a high solids aqueous TME solution, or to remove the crystallized material mechanically from the crystal-clogged equipment.

It is therefore an object of this invention to provide a method for inhibiting crystallization in supersaturated aqueous solutions of trimethylolethane.

It is a further object of this invention to provide crystallization-inhibited aqueous trimethylolethane solutions and a method for preparing those crystallization-inhibited solutions.

It is still a further object of this invention to identify materials useful as stabilizers for aqueous trimethylolethane solutions, and to provide a liquid, pumpable grade of aqueous high solids trimethylolethane solution exhibiting resistance to unwanted, premature crystallization of trimethylolethane from solution.

DETAILED DESCRIPTION OF THE INVENTION

In many respects, crystallization is more of an art than a science. Processes based on crystallization steps can be difficult to operate consistently. In some cases crystallizations which have been practiced commercially for extended periods of time can, without warning or explanation, encounter difficulties with recovered yields and with crystallization rates. These effects are probably due to trace impurities which inhibit the crystallization process. Generally little is known about these inhibitors but it is logical that the inhibitors somehow interfere with the crystallization process. Often crystallization inhibitors are found by accident and they are nearly always specific to each solid/solvent system. In the case of pentaerythritol, a close cousin of trimethylolethane, some crystallization inhibitors have been identified, including formaldehyde, sucrose, caustic and trimethylolethane itself.

The present invention is based on applicant's investigation of crystallization inhibitors for supersaturated aqueous trimethylolethane solutions. Of the more than 100 chemical compositions evaluated the following materials were found to be most active as crystallization inhibitors for supersaturated aqueous trimethylolethane solutions: methanol, isopropyl alcohol, 2-ethoxyethanol, 1-methoxy-2-propanol, formaldehyde (methanol inhibited), 1-dimethylamino-2-propanol, and formic acid. Of these compounds 1-dimethylamino-2-propanol and formaldehyde appeared to provide the highest degree of crystallization inhibition.

Thus in accordance with the present invention a method is provided for inhibiting crystallization of trimethylolethane from supersaturated aqueous solutions thereof. The method comprises forming the supersaturated solution in the presence of a crystallization inhibitor compound selected from the group consisting of methanol, formaldehyde, isopropyl alcohol, 2-ethoxyethanol, 1-methoxy-2-propanol, and 1-dimethylamino-2-propanol in an amount effective to inhibit trimethylolethane crystal formation. The crystallization inhibitor preferably forms between about 5 and about 15%, more preferably about 10 to about 15% of the resulting supersaturated aqueous trimethylolethane solution.

The above-identified crystallization inhibitors were identified experimentally by measuring the time needed for solidification on cooling of a 40% aqueous trimethylolethane solution in a freezer at 5° F. Test solutions at the 5% additive level were prepared by combining 2.5 grams of additive with 47.5 grams of a stock solution of 400 grams of trimethylolethane dissolved in 360 ml water. At the 10% level, 5 grams of test additive was combined with 45 grams of a stock solution of 352 grams of trimethylolethane dissolved in 440 ml water. Crystallization inhibitors were identified by those test solutions which failed to solidify after two hours in a freezer at 5° F. Formic acid (88%), 1-dimethylamino-2-propanol (DMA-2P) and formaldehyde (37% aqueous) wholly or partially prevented crystallization in the supersaturated trimethylolethane solution at the 5% level. Compounds found to be effective crystallization inhibitors at the 10% level were methanol, formic acid, 1-dimethylamino-2-propanol, formaldehyde (37%), isopropyl alcohol, 2-ethoxyethanol and 1-methoxy-2-propanol (Dowanol PM). Secondary-butyl alcohol, tertiary-butyl alcohol and 2-methoxyethanol were found to exhibit partial efficacy as a crystallization inhibitor of TME solutions at the 10% by weight level.

The mode of action of the crystallization inhibitors identified in accordance with the present invention is not well understood. However, they probably function as kinetic crystallization inhibitors. Based on available data the crystallization inhibitors identified are not good solvents for trimethylolethane relative to water. Interestingly a number of compounds closely related to those found having crystallization inhibitory activity were tested but found inactive. Among compounds showing no crystallization inhibitory activity are ethanol, n-butanol, isobutyl alcohol, 2-butoxyethanol, diethylene glycol monoethyl ether, Dowanol DPM (dipropylene glycol monomethyl ether) ethylene glycol, propylene glycol, and 1,3- and 1,4-butane diols. While it is believed that some form of hydrogen bonding process may be involved in trimethylolethane crystallization inhibition, the mechanism by which the process occurs is not known.

It should be pointed out that the effective crystallization inhibiting additives described herein do not totally prevent crystallization at all levels of supersaturation. The efficacy of the inhibitors is measured essentially in terms of delaying crystallization. Even with the most effective additives, TME crystallization could be effected at low temperatures (high supersaturation levels) with seeding. Nonetheless, identification of crystallization inhibitors in accordance with the present invention offers a significant advantage for commercial manufacture and shipment of easily handled TME in bulk liquid form.

I claim:

1. A method for inhibiting crystallization of trimethylolethane in a supersaturated aqueous solution thereof comprising forming said supersaturated solution in the presence of a crystallization inhibitor compound selected from the group consisting of isopropanol, s-butyl alcohol, t-butyl alcohol, 1-ethoxyethanol, 2-methoxyethanol, 1-methoxy-2-propanol, and 1-dimethylamino-2-propanol in an amount of from about 5% to about 15% by weight of the resulting solution.

2. The method of claim 1 wherein the crystallization-inhibitor forms about 10 percent by weight of the resulting crystallization inhibited supersaturated aqueous trimethylolethane solution.

3. The method of claim 1 wherein the crystallization-inhibitor compound is 1-dimethylamino-2-propanol.

4. The method of claim 3 wherein the crystallization-inhibitor compound forms about 5 percent by weight of the crystallization-inhibited supersaturated trimethylolethane solution.

5. A supersaturated aqueous solution of trimethylolethane containing about 5 to about 15 percent by weight of a crystallization-inhibitor compound selected from the group consisting of 2-ethoxyethanol, 1-methoxy-2-propanol, and 1-dimethylamino-2-propanol.

6. The trimethylolethane solution of claim 5 wherein the crystallization-inhibitor compound forms about 10 to about 15 percent by weight of the supersaturated aqueous solution.

7. The method of claim 1 wherein the crystallization-inhibitor compound is isopropyl alcohol.

* * * * *